(12) United States Patent
Sahashi

(10) Patent No.: US 6,644,236 B2
(45) Date of Patent: Nov. 11, 2003

(54) DETERIORATION INDICATOR AND A PRODUCT HAVING THE SAME

(75) Inventor: Toshiro Sahashi, Yokohama (JP)

(73) Assignee: Ricoh Company, Ltd., Tokyo (JP)

( * ) Notice: Subject to any disclaimer, the term of this patent is extended or adjusted under 35 U.S.C. 154(b) by 75 days.

(21) Appl. No.: 09/809,075

(22) Filed: Mar. 16, 2001

(65) Prior Publication Data

US 2001/0036666 A1 Nov. 1, 2001

(30) Foreign Application Priority Data

Mar. 16, 2000 (JP) .......................... 2000-073439
Feb. 16, 2001 (JP) .......................... 2001-039475

(51) Int. Cl.$^7$ .................. G01N 17/00; G01N 33/44
(52) U.S. Cl. .................. 116/202; 73/865.6; 29/402.11; 116/264
(58) Field of Search ................. 116/202, 264; 29/402.11; 73/865.6; 436/5; 422/55

(56) References Cited

U.S. PATENT DOCUMENTS

| | | | |
|---|---|---|---|
| 3,981,958 A | * | 9/1976 | Nakashima et al. |
| 4,098,121 A | | 7/1978 | Captain ................ 73/337 |
| 4,499,849 A | | 2/1985 | Tomita ................ 118/652 |
| 4,547,059 A | | 10/1985 | Nagayama et al. ..... 198/806 X |
| 4,571,070 A | | 2/1986 | Tomita et al. ................ 355/15 |
| 4,655,076 A | | 4/1987 | Weihe et al. ................ 73/73 |
| 4,912,162 A | * | 3/1990 | Kishida et al. ................ 525/67 |
| 5,105,222 A | | 4/1992 | Ohta et al. ................ 355/211 |
| 5,121,168 A | | 6/1992 | Aoki et al. ................ 355/298 |
| 5,592,267 A | | 1/1997 | Misago et al. ................ 399/62 |
| 5,638,159 A | | 6/1997 | Kai et al. ................ 399/253 |
| 5,815,784 A | | 9/1998 | Kasahara et al. ........... 399/358 |
| 5,875,380 A | | 2/1999 | Iwata et al. ................. 399/301 |
| 5,878,317 A | | 3/1999 | Masuda et al. ............. 399/359 |
| 5,895,843 A | | 4/1999 | Taylor et al. ................ 73/86 |
| 5,953,567 A | | 9/1999 | Muramatsu et al. ........ 399/256 |
| 5,987,298 A | | 11/1999 | Muramatsu et al. ........ 399/359 |
| 6,112,046 A | | 8/2000 | Suzuki et al. ............... 399/359 |
| 6,122,468 A | | 9/2000 | Sakamoto et al. .......... 399/223 |
| 6,128,459 A | | 10/2000 | Iwata et al. ................. 399/301 |
| 6,142,690 A | | 11/2000 | Yoshimura et al. ...... 400/636.2 |
| 6,163,669 A | | 12/2000 | Aoki et al. ................. 399/159 |
| 6,201,941 B1 | | 3/2001 | Kasahara et al. ........... 399/258 |
| 6,249,304 B1 | | 6/2001 | Sawayama et al. ......... 347/228 |
| 6,282,396 B1 | | 8/2001 | Iwata et al. ................. 399/301 |
| 6,295,437 B1 | | 9/2001 | Hodoshima et al. ........ 399/346 |
| 6,381,435 B2 | | 4/2002 | Shinohara et al. .......... 399/301 |
| 6,393,241 B1 | | 5/2002 | Matsumoto et al. ........ 399/258 |
| 6,505,022 B2 | | 1/2003 | Kosuge et al. .............. 399/159 |
| 6,507,720 B2 | | 1/2003 | Kabumoto et al. ......... 399/258 |
| 2002/0037189 A1 | | 3/2002 | Kosuge ....................... 399/350 |
| 2002/0039502 A1 | | 4/2002 | Matsumoto et al. ........ 399/258 |

(List continued on next page.)

FOREIGN PATENT DOCUMENTS

| | | | | |
|---|---|---|---|---|
| FR | 2683637 | * | 5/1993 | ................ 73/86 |
| JP | 3-215744 | * | 9/1991 | ......... G01N/33/44 |
| JP | 7-55788 | | 3/1995 | |
| JP | 7-306239 | | 11/1995 | |
| JP | 6-273326 | * | 9/1997 | ............. 250/356.2 |
| JP | 10-240081 | | 9/1998 | |
| JP | U3064497 | | 9/1999 | |
| JP | 11-258187 | * | 9/1999 | ......... G01N/33/44 |
| JP | 2000-314688 | * | 11/2000 | ......... G01N/33/44 |
| JP | 2002-22648 | * | 1/2002 | ......... G01N/17/00 |
| WO | WO 99/61889 | | 12/1999 | |

*Primary Examiner*—Thomas P. Noland
(74) *Attorney, Agent, or Firm*—Oblon, Spivak, McClelland, Maier & Neustadt, P.C.

(57) ABSTRACT

A deterioration indicator for a resin mold member in a product includes a deteriorating state checking portion configured to allow evaluation of a deterioration state of the resin mold member. The deteriorating state checking portion includes a material whose weather resistance value, $\Delta E$, is less than a weather resistance value, $\Delta E$, of the resin mold member.

22 Claims, 6 Drawing Sheets

U.S. PATENT DOCUMENTS

| | | | |
|---|---|---|---|
| 2002/0114646 A1 * | 8/2002 | Sudo et al. | 399/258 |
| 2002/0135655 A1 * | 9/2002 | Ameyama et al. | 347/129 |
| 2002/0197549 A1 * | 12/2002 | Sakon et al. | 430/66 |
| 2003/0016966 A1 * | 1/2003 | Hattori et al. | 399/258 |
| 2003/0038968 A1 * | 2/2003 | Kawaura | 358/1.15 |
| 2003/0044185 A1 * | 3/2003 | Kawaura | 379/8 |
| 2003/0044201 A1 * | 3/2003 | Kosuge | 399/223 |

* cited by examiner

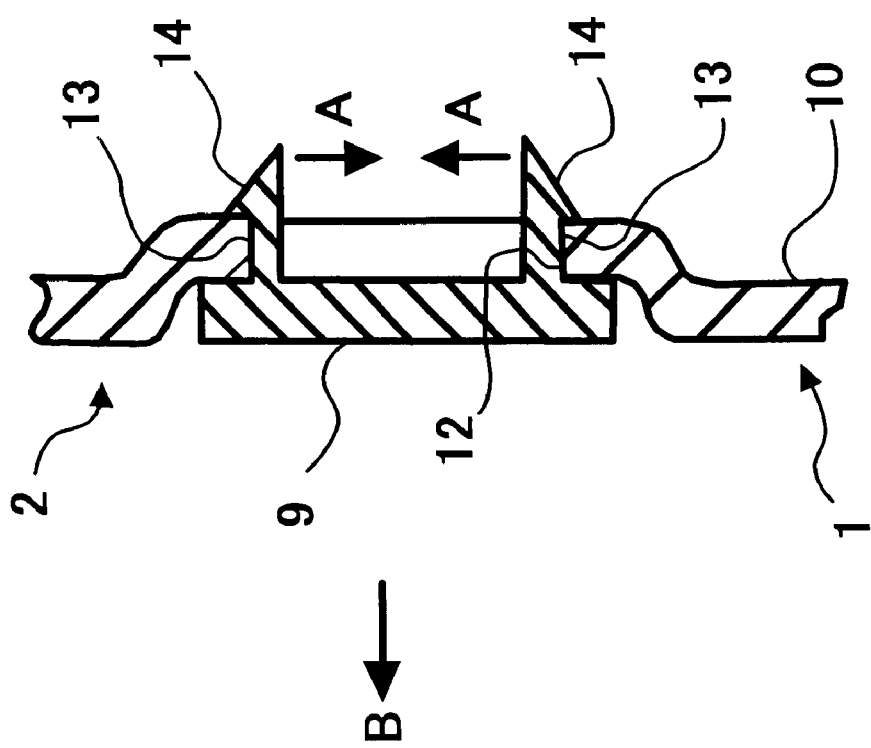

DETERIORATION INDICATOR AND A PRODUCT HAVING THE SAME

CROSS-REFERENCE TO RELATED APPLICATIONS

The present application claims priority to Japanese Patent Application Nos. 2000-073439 filed on Mar. 16, 2000 and 2001-039475 filed on Feb. 16, 2001 in the Japanese Patent Office. The contents of those applications are incorporated herein by reference in their entirety.

BACKGROUND OF THE INVENTION

1. Field of the Invention

The present invention relates to a deterioration indicator and a product having at least one resin mold member and a deterioration indicator therefor.

2. Discussion of the Background

Presently, most of industrial products on market, as a part or the whole, include a resin mold member regardless of whether such industrial products are a finished product or a part thereof. When a product has such a resin mold member finishes, for the sake effective use of resources, the product is often recycled. Generally, there are two types of recycling, one case where a used product is used again as it is, and the other case used where a product is disassembled and refurbished for the next use. In the first type of recycling, for example, a resin mold member of a used product is broken into pieces and a new product is produced by using the pieces as the material In the first type of recycling, a product is not broken into pieces, but instead cleaned according to necessity. Thus, the product can be used as a new product again. A used product may be also recycled as resources in some cases. For example, it may be recycled as fuel by burning and utilizing its heat.

Because of the simplicity of processing and the cost of recycling, the first type of recycling is more desirable. However, when a product has been exposed to a sunlight or a rain water etc. while being used or transported etc., the product deteriorates such that the mechanical property or the appearance etc. may be greatly deteriorated. In such a case, the first type of recycling cannot be realized, but instead the product must be recycled as material for producing the product or as a fuel source.

When a product is recycled, several processing methods described above exist. Therefore, to determine a suitable processing of recycling, the deteriorating state of a used product is considered properly.

However, it is difficult to visually determine to what degree a resin mold member has been deteriorated, and therefore it is difficult to instantly determine a suitable recycling processing for a used product.

Japanese Laid Open Patent Publication No. 10-240081 discloses a method in which the number of times used with respect to an apparatus or a member of a product for recycling is recorded, and the record is used as data for determining a suitable recycling processing. However, according to that method, a structure of the product becomes complicated.

SUMMARY OF THE INVENTION

According to one aspect of the present invention, a deterioration indicator for a resin mold member in a product includes a deteriorating state checking portion configured to allow evaluation of a deterioration state of the resin mold member. The deteriorating state checking portion includes a material whose weather resistance value, $\Delta E$, is less than a weather resistance value, $\Delta E$, of the resin mold member.

According to another aspect of the present invention, a deterioration indicator for a resin mold member in a product includes a deteriorating state checking device configured to allow evaluation of a deterioration of the resin mold member. The deteriorating state checking device includes a storing portion configured to permit water to enter and a capacity changing material provided in the storing portion and configured to change capacity when the capacity changing material absorbs water.

According to yet another aspect of the present invention, a method of checking a deteriorating state of a resin member in a product includes providing a deteriorating state checking portion configured to allow an evaluation of a deteriorating state of the resin member, the deteriorating state checking portion including a material whose weather resistance value, $\Delta E$, is smaller than a weather resistance value, $\Delta E$, of the resin mold member, and evaluating the deteriorating state of the resin member by checking the deteriorating state checking portion.

According to still another aspect of the present invention, a method of checking a deteriorating state of a resin mold member in a product includes providing a deteriorating checking device including a capacity changing material configured to change capacity when the capacity changing material absorbs water, and checking the deteriorating state of the resin mold material by observing the deteriorating checking device.

According to still another aspect of the present invention, a method of recycling a product having a resin mold material includes providing a deteriorating state checking portion including a material whose weather resistance value, $\Delta E$, is smaller than a weather resistance value, $\Delta E$, of the resin mold material, checking a deteriorating state of the deteriorating state checking portion, and replacing the deteriorating state checking portion of the product with a new deteriorating state checking portion when the product is recycled.

According to yet still another aspect of the present invention, a method of recycling a product having a resin mold member includes providing a deteriorating checking device including a capacity changing material configured to change capacity when the capacity changing material absorbs water, checking a deteriorating state of the resin mold member by evaluating the deteriorating checking device, and replacing the capacity changing material with a new capacity changing material when the product is recycled.

BRIEF DESCRIPTION OF THE DRAWINGS

A more complete appreciation of the present invention and many of the attendant advantages thereof will be readily obtained as the same becomes better understood by reference to the following detailed description when considered in conjunction with accompanying drawings, wherein:

FIG. 2 is an enlarged cross-section view of a front cover in the image forming apparatus shown in FIG. 1;

DESCRIPTION OF THE PREFERRED EMBODIMENTS

Figure 1:
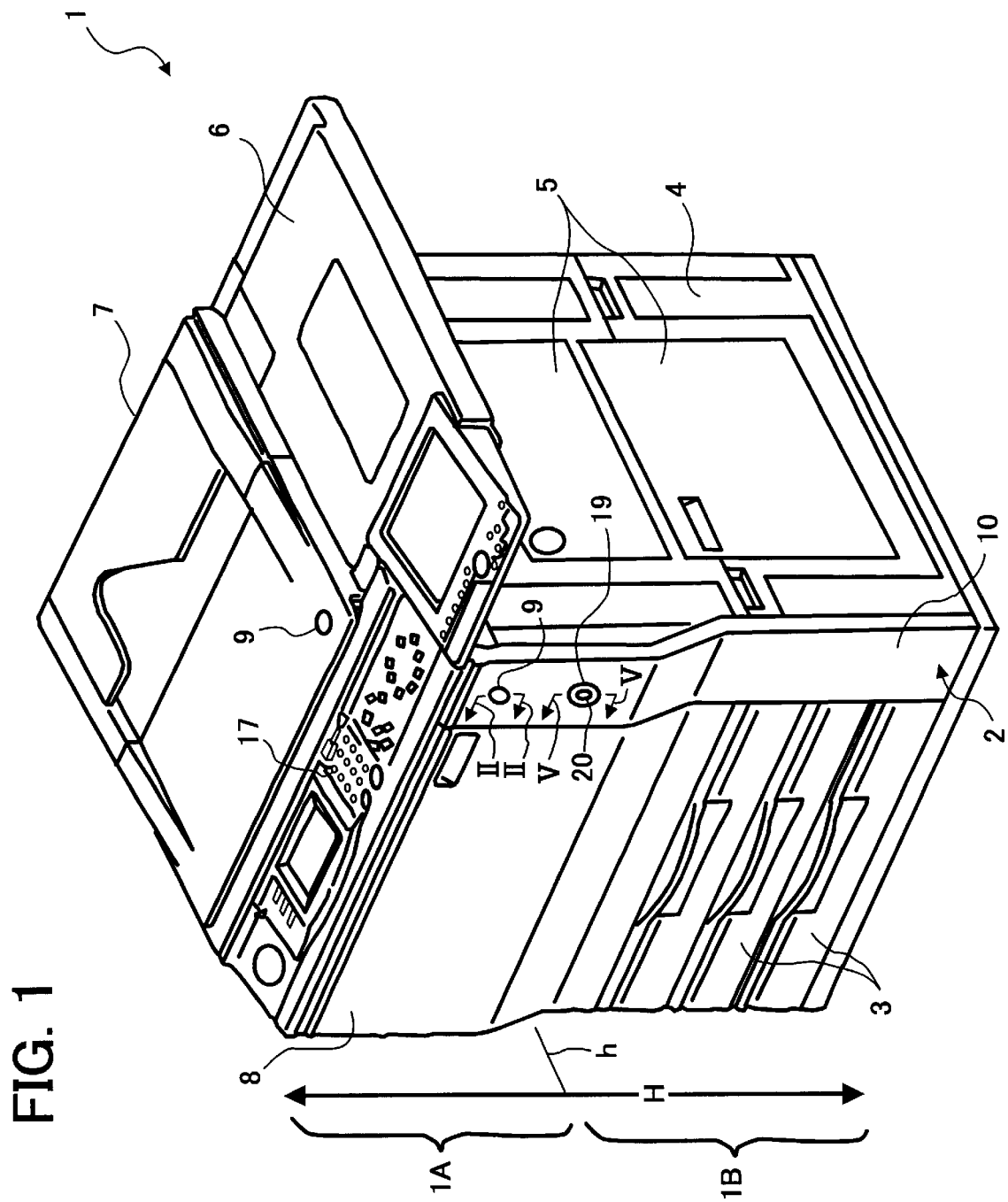
FIG. 1 is a perspective view of an image forming apparatus having a deterioration indicator according to one embodiment of the present invention.

Referring now to the drawings, wherein like reference numerals designate identical or corresponding parts throughout the several views, preferred embodiments of the present invention are described.

The present invention can be applied to any products, for example, an image forming apparatus such as a copying machine, other electric products, vehicles, measurement equipments, household products, furniture, toys, and various parts used in these machine and products. However, as an embodiment of the present invention, an exterior cover of an image forming apparatus will be described hereinafter.

FIG. 1 is a perspective view of a copying machine. An exterior cover 1 of the copying machine includes a front cover 2 positioned at a front side of the apparatus, a front door 8, a paper feeding tray cover 3, a side cover 4 positioned at a right side of the apparatus, a side cover positioned at a left side opposite to the right side of the apparatus, an upper cover 6 positioned at an upper side of the apparatus, and a pressing board 7 for pressing a document positioned on the upper cover 6.

The exterior cover 1 is made of a resin mold member, and a deteriorating state checking portion is provided in the exterior cover 1. In the embodiment illustrated in FIG. 1, the deteriorating state checking portion 9 is formed in the front cover 2 and an upper surface of the pressing board 7, respectively. However, the deteriorating state checking portion 9 can be formed in any other cover members. Describing the front cover 2 as an example, the front cover 2 has a resin mold member 10 which is a body of the front cover 2 and the deteriorating state checking portion 9 which is installed in the resin mold member 10 is exposed to an outside. The deteriorating state checking portion 9 is made of a material whose weather resistance is worse than the resin mold member 10 of the front cover 2 and other cover members. When the resin mold member 10 and the deteriorating state checking portion 9 are exposed to sunlight for the same duration, the deteriorating state checking portion 9 changes its color more remarkably than the resin mold member 10. The pressing board 7 includes another deteriorating state checking portion 9 in the substantially same manner as the front cover 2. In the description below, the resin mold member of each cover member other than the front cover 2 is also designated by Reference Numeral 10.

When the image forming apparatus is no longer used by a user, the used image forming apparatus is transported to a recycling dealer. Then, as described above, it is determined whether the exterior cover 1 can be recycled as itself, a material or resources.

The environment in which an image forming apparatus is used by a user varies. The image forming apparatus may have been used under severe condition in some cases. Also, when the image forming apparatus is being transported to a recycling dealer, the apparatus may have been roughly handled and exposed to much sunlight or rain in some cases. When the image forming apparatus has been put under such a condition, the mechanical property of the exterior cover 1 such as tensile strength, impact strength, bending strength or the appearance such as glossiness is greatly reduced. In this case, it is not proper to recycle each member of the exterior cover 1 as it is. Therefore, the exterior cover 1 is recycled as a material for a new product or resources. Only when the exterior cover 1 has not deteriorated excessively, the exterior cover is recycled as it is.

In determining whether the exterior cover 1 is recycled as itself, a material or resources, the deteriorating state checking portion 9 described above is used. As described above, the deteriorating state checking portion 9 is made of a material whose weather resistance is worse than the resin mold member 10 of the exterior cover 1. By visually recognizing the color of the deteriorating state checking portion 9, one can instantly evaluate under what environment the resin mold member 10 has been put or to what degree the resin mold member 10 has deteriorated, thereby determining a suitable processing method for the exterior cover 1 instantly. Once the color of the deteriorating state checking portion 9 changes, it does not return to its original color. Therefore, the deterioration of the resin mold member 10 can be correctly understood. Thereby, one can easily evaluate to what degree the exterior cover 1 has been exposed to an outside simply by observing the color change of the deteriorating state checking portion 9 without performing complicated work to measure the mechanical property of the resin mold member with a measurement equipment.

As described above, a product whose deteriorating state can be recognized, for example, includes an exterior cover 1 in the above embodiment having the resin mold member and the deteriorating state checking portion whose weather resistance is worse than the resin mold member. With such a structure, the deteriorating state of the resin mold member can be easily and effectively found out without a large cost increase of the product.

Generally, if a resin mold member is put under a severe condition by being exposed to sunlight or rain, etc., the color of the resin mold member changes. Therefore, the color difference, $\Delta E$ between the color of the resin mold member before and after being exposed to a certain condition is defined as a weather resistance, $\Delta E$, of the resin mold member. Smaller the weather resistance, $\Delta E$, is, higher the weather resistance of the resin mold member 10 is. By making the resin mold member 10 of each cover member with the material whose weather resistance value is less than 2, the weather resistance, $\Delta E$, of the exterior cover 1 can be made high. On the other hand, if the weather resistance, $\Delta E$, of the deteriorating state checking portion 9 is set to 4 or more, because the color change of the deteriorating state checking portion becomes more remarkable by a severe condition under which the exterior cover 1 is put, the deteriorating state of the resin mold member 10 can be more properly recognized. For example, by making the resin mold member 10 with ABS resin whose weather resistance, $\Delta E$, is 1.2 and the deteriorating state checking portion 9 with a resin whose weather resistance, $\Delta E$, is 4.6, the difference between the weather resistances, $\Delta E$, is made large.

As described above, by making a resin mold member with a material whose weather resistance, $\Delta E$, is less than 2 and a checking portion of deteriorating state with a material whose weather resistance, $\Delta E$, is 4 or more, a product whose deteriorating state is more recognizable can be provided.

The deteriorating state checking portion 9 can be integrally formed with the resin mold member 10. However, when the exterior cover 1 is recycled as it is, the exterior cover 1 is used as an exterior cover of a new image forming apparatus, again. Therefore, when the new image forming apparatus has been used to the end, it needs to be determined whether the exterior cover 1 can be further recycled as it is or should be recycled as a material or resources by checking the deteriorating state of the exterior cover 1, using the deteriorating state checking portion 9.

Therefore, by making the deteriorating state checking portion 9 as a member detachable from the resin mold member 10, when the exterior cover 1 is recycled as it is, the deteriorating state checking portion 9 can be removed from the resin mold member 10 and a new deteriorating state checking portion 9 can be installed to the resin mold member 10 to be recycled as it is. Thereby, when the image forming apparatus has been used up again, it can be easily determined whether the exterior cover 1 can be further recycled as it is or should be recycled as a material or resources by visually checking the deteriorating state checking portion 9 of the exterior cover 1.

In order to install the deteriorating state checking portion 9 to the resin mold member 10 in a detachable manner, an installing hole 12, for example, is formed in the resin mold member 10 as illustrated in FIG. 2. Elastic leg portions 13 formed in the deteriorating state checking portion 9 are inserted into the installing hole 12, and nail portions 14 on the tips of the leg portions 13 are configured so as to engage with edge portions of the installing hole 12. When the deteriorating state checking portion 9 is removed, the leg portions 13 are elastically changed in directions indicated by Arrows (A), and the nail portions 14 are removed from the edge portions of the installing hole 12, and further the deteriorating state checking portion 9 is pulled out to an outside as indicated by Arrow (B).

While using an image forming apparatus or when being carried from its user to a recycling dealer, an upper portion of the exterior cover 1 is more likely to be exposed to sunlight or rain than a lower portion thereof. Therefore, by forming the deteriorating state checking portion 9 in the upper portion of the exterior cover 1 rather than in the lower portion of the exterior cover 1 as illustrated in FIG. 1, the deteriorating state of the exterior cover 1 is evaluated more correctly. As illustrated in FIG. 1, when a product, for example, the exterior cover 1 in the embodiment, is put in an ordinary use and when the product is divided into an upper portion 1A and a lower portion 1B divided by a middle height position (h) of the whole height (H), the deteriorating state checking portion 9 may be formed to be exposed to the outside at the upper portion 1A of the upper portion 1A and the lower one 1B. Thereby, the deteriorating state of the product is more accurately recognizable.

Figure 4:
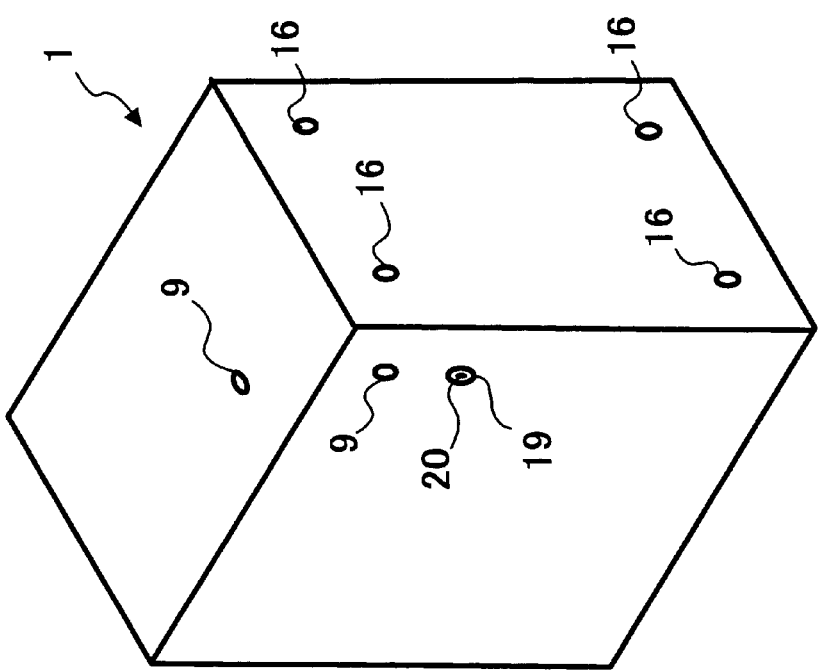
FIG. 4 is a perspective view of the image forming apparatus in FIG. 3 without a peripheral.
Figure 3:
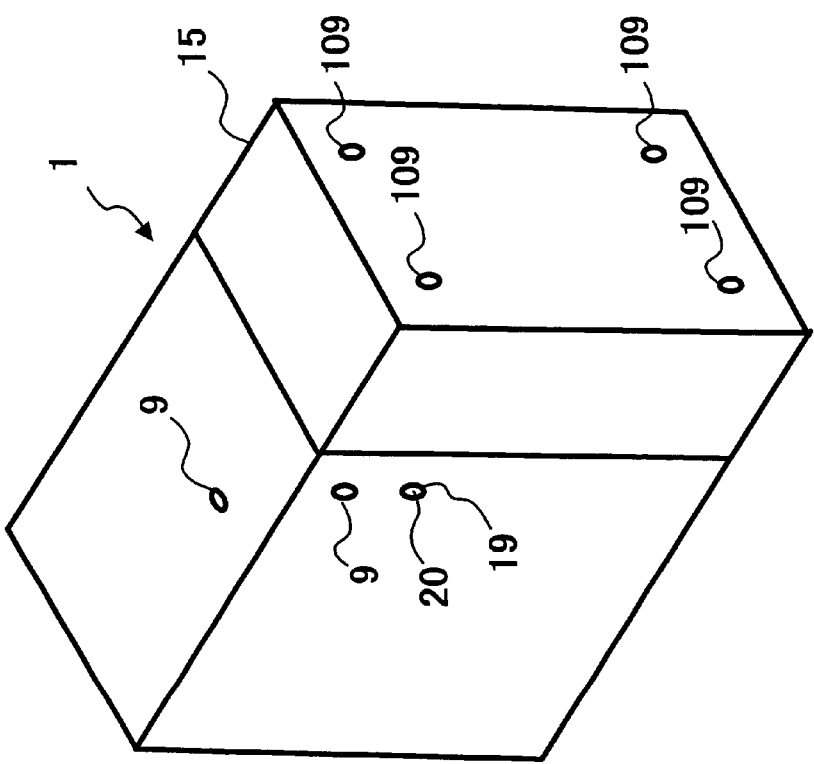
FIG. 3 is a perspective view of the image forming apparatus in FIG. 1 with a peripheral.

As illustrated in FIG. 3, in an apparatus such an image forming apparatus, a peripheral equipment such as a gathering machine and a stapler is connected to the exterior cover 1 in some cases. In such a case, as illustrated in FIG. 4, in the resin mold member of the exterior cover 1, installing holes 16 for connecting the peripheral equipment 15 (see FIG. 3) are formed. Generally, the peripheral equipment 15 is installed as user desires. Therefore, when the user does not so desire, the peripheral equipment is not connected to the image forming apparatus. When the peripheral equipment is not connected, the installing holes 16 exposed to the outside reduce the appearance. Therefore, a cap is often set to each of the installing holes 16.

However, by installing the deteriorating state checking portion 9 in the installing holes 16, such a cap is not necessary or less caps are used. In addition, an installing hole for installing the deteriorating state checking portion 9 does not need to be formed in other parts of the exterior cover 1, thereby reducing the cost of the image forming apparatus. When the peripheral equipment 15 is connected, the deteriorating state checking portion 109 can be installed in the peripheral equipment 15 as well, as shown in FIG. 3. Such a structure can be also applied to a case where a product other than the peripheral equipment is connected to the exterior cover 1.

As described above, when the installing hole 16 is formed in a resin mold member of a product for attaching a peripheral product other than the product having the resin mold member, the cost of the product can be decreased by installing the deteriorating state checking portion 9 in the installing hole 16.

In the embodiment described above, the deteriorating state checking portion 9 is formed exclusively for recognizing the deteriorating state of the resin mold member. However, the deteriorating state checking portion 9 can be also an original member necessary in a product, for example, an operation button 17 in an image forming apparatus as illustrated in FIG. 1.

As described above, when a used image forming apparatus is carried to a recycling dealer, the apparatus is often handled roughly. For example, the apparatus is left in a place with no roof and the exterior cover 1 is directly exposed to rain in some cases. In such a case, the exterior cover 1 deteriorates faster. Therefore, in order to surely recognize that the exterior cover 1 has been exposed to rain, it is preferable that the exterior cover 1 is made as described below.

Figure 5:
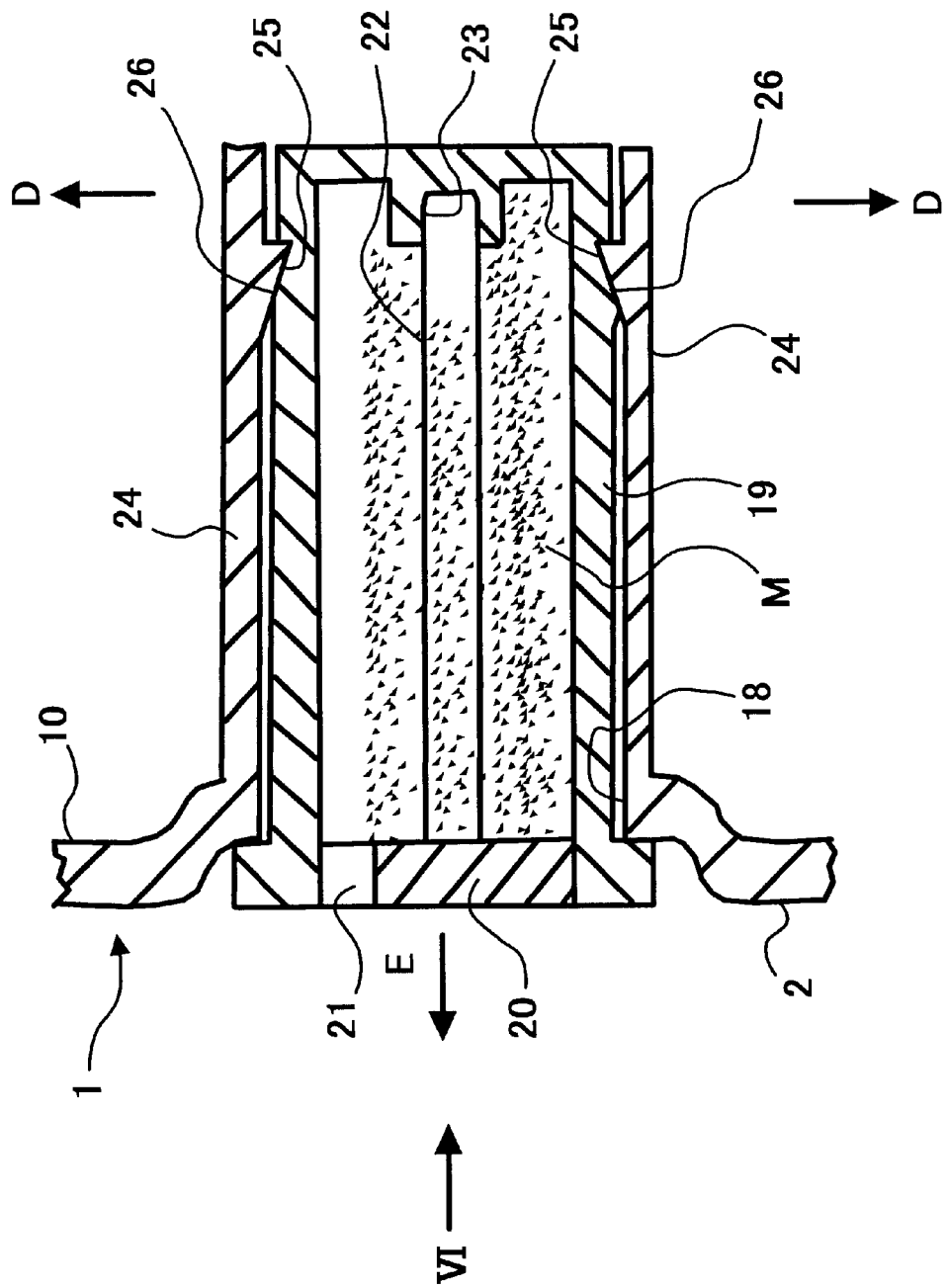
FIG. 5 is an enlarged section view of an exterior cover in the image forming apparatus shown in FIG. 1.
Figure 6:
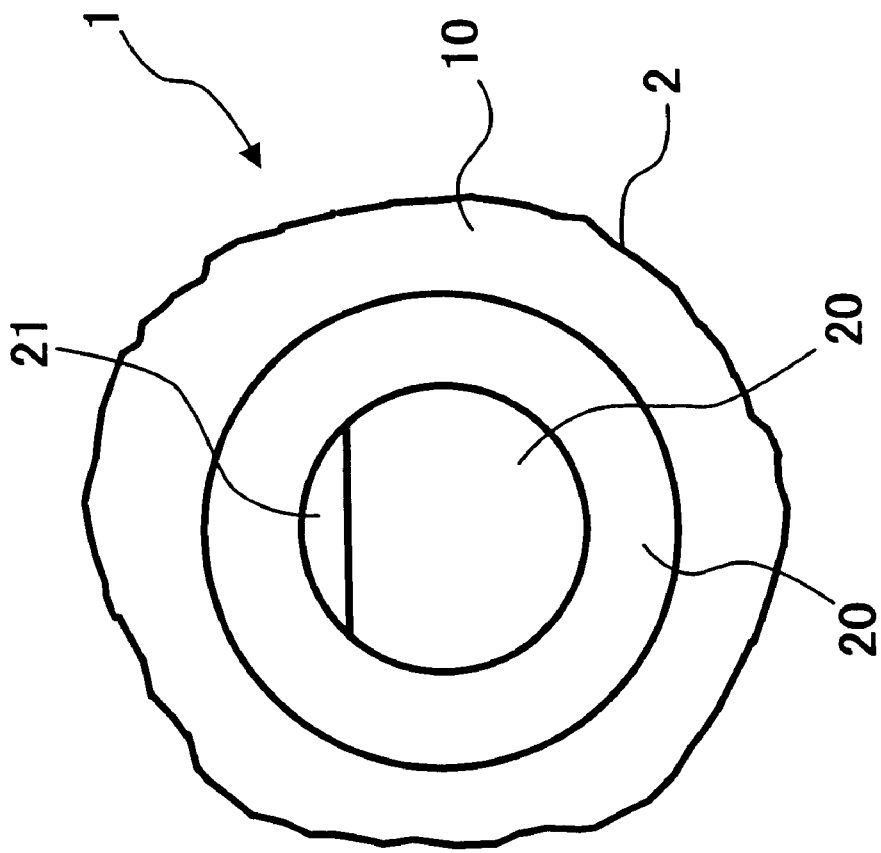
FIG. 6 is an enlarged section view of an exterior cover in the image forming apparatus seen from a direction indicated by Arrow VI in FIG. 5.

FIG. 5 is an enlarged section view of an exterior cover in the image forming apparatus shown in FIG. 1 and FIG. 6 is a view from the direction indicated by Arrow IV in FIG. 5. As illustrated in FIGS. 5 and 6, a storing case 19 engages with an installing hole 18 which is formed in the resin mold member 10 of the exterior cover 1. In a storing portion of the storing case 19, a capacity changing material (M) which changes its capacity by absorbing water is enclosed. An opening of the storing case 19 is closed except an upper portion thereof by a cap 20, and the capacity changing material (M) in the storing case 19 can be seen through a gap 21 in the upper portion of the opening. An end portion of a supporting rod 22 is fixed to the cap 20 and a tip portion of the supporting rod 22 is engaged with a concave portion 23 which is formed in a bottom portion of the storing case 19 so that the cap is prevented from being removed from the opening. The capacity changing material (M) is a kind of material that, after absorbing water and changing its capacity, the capacity of the material is maintained even if the water is evaporated and removed from it. For example, the capacity changing material (M) may be a powder whose capacity decreases by absorbing the water.

When a used image forming apparatus is carried to a recycling dealer, if the image forming apparatus is exposed to rain, water enters inside the storing case 19 through the gap 21. Thereby, the capacity changing material (M) absorbs the water and the capacity decreases. Unless the image forming apparatus is exposed to rain, the capacity of the capacity changing material (M) does not change. Therefore, when the recycling dealer determines a suitable recycling method of the exterior cover 1, she can immediately recognize whether the exterior cover 1 has been exposed to rain by looking into the inside of the storing case 19 to check whether the capacity changing material (M) has been decreased in its capacity.

As described above, the capacity changing material (M) which changes its capacity by absorbing water is provided in a resin mold member of a product. The capacity changing material (M) is stored in a storing portion where water is allowed to enter and the capacity changing material (M) can be seen from the outside. Thereby, it is easily recognized whether the resin mold member is exposed to rain, thereby permitting the deterioration to be noticeable.

Figure 7:
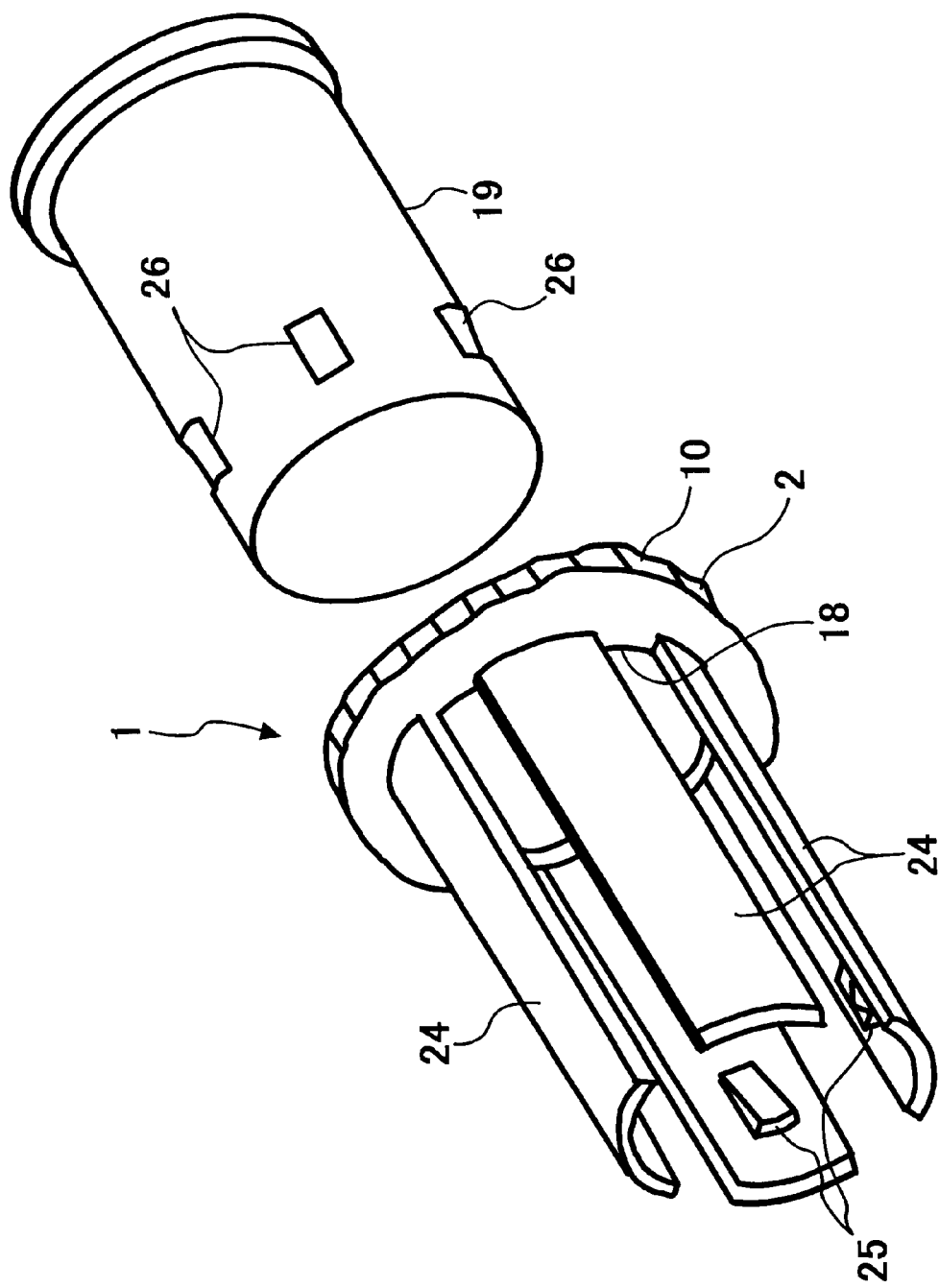
FIG. 7 is a perspective view of a storing case containing capacity changing material installed to a resin mold member according to an embodiment of the present invention.

In the case of the capacity changing material (M), as in the case of the deteriorating state checking portion 9, when a product, for example, the exterior cover 1 in this embodiment, is put under an ordinary use and when it is divided into an upper portion 1A and a lower portion 1B divided by a middle height position (h) of the whole height (H), it is preferred that the capacity changing material (M) is provided at least in the upper portion 1A of an upper portion 1A and a lower portion 1B, A storing portion which stores the capacity changing material (M) may be formed in the resin mold member 10 itself such that the storing portion is a part of the resin mold member 10. However, by making the storing portion for the capacity changing material (M) a storing case 19 which is detachably installed to the resin mold member 10, the deteriorating state checking portion 9 is detachably installed to the resin mold member 10 as described in the above embodiment. In this case, as illustrated in FIGS. 5 and 7, in an inner surface of the resin mold member 10 around the installing hole 18, elastic guides 24 are formed. In addition, nails 25 are formed in the surfaces of the elastic guides 24 facing each other. The storing case 19 is inserted into the installing hole 18 as illustrated in FIG. 5, an engaging groove 26 formed in an outer circumference portion of the storing case 15 is engaged with the nail 25, and the storing case 19 is fixed to the resin mold member 10. When the storing case 19 is removed from the resin mold member 10, the elastic guides 24 elastically changes in an enlarging direction as indicated by Arrow (D) in FIG. 5, the nails 25 are removed from the engaging groove 26, and the storing case 19 is pulled out to the outside as indicated by Arrow (E), in FIG. 5.

Further, as illustrated in FIGS. 3 and 4, when the installing hole 16 for installing a peripheral product other than a product having a mold member is formed in a resin mold member of the product, the storing case 19 as illustrated in FIG. 5 can be installed to the installing hole 16 when the peripheral equipment 15 is not connected. Thereby, a cap for covering the installing hole 16 is not necessary, or less caps are needed. Further, the installing hole exclusively for installing the storing case 19 does not need to be formed in the resin mold member.

The exterior cover of an apparatus such as an image forming apparatus is easily exposed to sunlight or rain, and therefore the present invention can be applied to the exterior covers of various products. However, as described above, the present invention applies to any products which are made of only a resin mold member or products including a resin mold member in their parts regardless of whether the products are a finished product or a part thereof.

According to one aspect of the present invention, the deteriorating state of a resin mold member can be recognized simply by eyes.

Further, according to another aspect of the present invention, a deteriorating state checking portion is easily exchangeable.

Furthermore, according to another aspect of the present invention, an installing hole exclusively for installing the deteriorating state checking portion does not need to be formed in the resin mold member.

According to yet another aspect of the present invention, a storing case for storing the deteriorating checking portion is easily exchangeable.

According to still another aspect of the present invention, an installing hole exclusively for installing the storing case does not need to be formed.

Numerous additional modifications and variations of the present invention are possible in light of the above teachings. It is therefore to be understood that within the scope of the appended claims, the present invention may be practiced otherwise than as specifically described herein.

What is claimed as new and is desired to be secured by Letters Patent of the United States is:

1. A deterioration indicator for a resin mold member in a product, comprising a deteriorating state checking portion configured to allow visible evaluation of a deterioration state of the resin mold member, said deteriorating state checking portion including a material whose weather resistance value, $\Delta E$, is less than a weather resistance value, $\Delta E$, of the resin mold member,
  wherein the deteriorating state checking portion is provided in an installing hole formed in the resin mold member for installing a peripheral product to the product.

2. The deterioration indicator of claim 1, wherein the deteriorating state checking portion is exposed to an outer surface of the product.

3. The deterioration indicator of claim 1, wherein the weather resistance value, $\Delta E$, of the material in the deteriorating state checking portion is 4 or more when the resin mold member comprises a material whose weather resistance value, $\Delta E$, is less than 2.

4. The deterioration indicator of claim 1, the deteriorating state checking portion is detachably provided in the resin mold member.

5. The deterioration indicator of claim 1, wherein when the product has an upper portion and a lower portion with respect to a middle height position of a total height thereof, the deteriorating state checking portion is formed at least in the upper portion of the product.

6. The deterioration indicator of claim 5, wherein the deteriorating state checking portion is exposed to an outer surface of the product.

7. The deterioration indicator of claim 1, wherein the deteriorating state checking device is provided in an exterior cover of the product.

8. An image forming apparatus comprising the deterioration indicator of claim 1.

9. A method of checking a deteriorating state of a resin member in a product, comprising the steps of:
  providing a deteriorating state checking portion configured to allow visible evaluation of a deteriorating state of the resin member, the deteriorating state checking portion including a material whose weather resistance value, $\Delta E$, is smaller than a weather resistance value, $\Delta E$, of the resin mold member; and
  visibly evaluating the deteriorating state of the resin member by checking the deteriorating state checking portion,
  wherein the step of providing the deteriorating state checking portion comprises providing the deteriorating state checking portion in an installing hole formed in the resin mold member for installing a peripheral product to the product.

10. The method of claim 9, wherein the step of providing the deteriorating state checking portion comprises providing the deteriorating state checking portion such that providing the deteriorating state checking portion is exposed on an outer surface of the product.

11. The method of claim 9, wherein the step of providing the deteriorating state checking portion comprises providing the material whose weather resistance value, $\Delta E$, is 4 or more when a weather resistance value, $\Delta E$, of the resin mold member is less than 2.

12. The method of claim 9, wherein the step of providing the deteriorating state checking portion comprises detachably providing the deteriorating state checking portion in the resin mold member.

13. The method of claim 9, wherein when the product is divided into an upper portion and a lower portion with respect to a middle height position of a total height thereof, the step of providing the deteriorating state checking portion comprises forming the deteriorating state checking portion at least in the upper portion of the product.

14. The method of claim 13, wherein the step of providing the deteriorating state checking portion comprises providing the deteriorating state checking portion such that the deteriorating state checking portion is exposed on an outer surface of the product.

15. The method of claim 9, wherein the step of providing the deteriorating state checking portion comprises providing the deteriorating state checking portion in an exterior cover of the product.

16. A method of recycling a product having a resin mold material, comprising:

providing a deteriorating state checking portion including a material whose weather resistance value, $\Delta E$, is smaller than a weather resistance value, $\Delta E$, of the resin mold material;

visibly checking a deteriorating state of the deteriorating state checking portion; and replacing the deteriorating state checking portion of the product with a new deteriorating state checking portion when the product is recycled, wherein the step of providing a deteriorating state checking portion comprises providing the deteriorating state checking portion in an installing hole formed in the resin mold member for installing a peripheral product to the product.

17. The method of claim 16, wherein the step of providing a deteriorating state checking portion comprises providing the deteriorating state checking portion such that the deteriorating state checking portion is exposed on an outer surface of the product.

18. The method of claim 16, wherein the step of providing a deteriorating state checking portion comprises providing the material whose weather resistance value, $\Delta E$, is 4 or more when a weather resistance value, $\Delta E$, of the resin mold member is less than 2.

19. The method of claim 16, wherein the step of providing a deteriorating state checking portion comprises detachably providing the deteriorating state checking portion in the resin mold member.

20. The method of claim 16, wherein when the product is divided into an upper portion and a lower portion with respect to a middle height position of a total height thereof, the step of providing a deteriorating state checking portion comprises forming the deteriorating state checking portion at least in the upper portion.

21. The method of claim 20, wherein the step of providing a deteriorating state checking portion comprises providing the deteriorating state checking portion such that the deteriorating state checking portion is exposed on an outer surface of the product.

22. The method of claim 16, wherein the step of providing a deteriorating state checking portion comprises providing the deteriorating checking portion in an exterior cover of the product.

* * * * *